US00PP31316P2

(12) United States Plant Patent
NeSmith

(10) Patent No.: US PP31,316 P2
(45) Date of Patent: Jan. 7, 2020

(54) SOUTHERN HIGHBUSH BLUEBERRY PLANT NAMED 'TH-1321'

(50) Latin Name: *Vaccinium corymbosum*
Varietal Denomination: TH-1321

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/350,824

(22) Filed: Jan. 17, 2019

(51) Int. Cl.
*A01H 5/08* (2018.01)
*A01H 6/36* (2018.01)

(52) U.S. Cl.
USPC ..... Plt./157
CPC ..... *A01H 6/36* (2018.05)

(58) Field of Classification Search
USPC ..... Plt./157
CPC ..... A01H 5/08
See application file for complete search history.

*Primary Examiner* — Kent L Bell
(74) *Attorney, Agent, or Firm* — Klarquist Sparkman, LLP

(57) ABSTRACT

The new variety 'TH-1321' ripens around mid-April in southeastern Georgia. The fruit of the new variety 'TH-1321' are very large, firm, have good flavor and scar. The new variety 'TH-1321' is vigorous with an estimated chilling requirement of about 50 to 100 hours at or below approximately 7° C. The asexually reproduced variety is reliably propagated vegetatively.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-1321' is a southern highbush blueberry plant that is a *Vaccinium corymbosum.*

Variety denomination: The new southern highbush blueberry plant claimed is of the variety denominated 'TH-1321'.

BACKGROUND OF THE INVENTION

The present invention relates to the discovery of a new and distinct cultivar of southern highbush blueberry plant botanically known as a *Vaccinium corymbosum* and herein referred to as 'TH-1321', as herein described and illustrated.

The new blueberry plant variety 'TH-1321' was selected in Griffin, Ga. in 2010. The new variety 'TH-1321' ripens around mid-April in southern Georgia. The fruit of the new variety 'TH-1321' are large with favorable firmness and good flavor. The new variety 'TH-1321' has acceptable yield and is vigorous with an estimated chilling requirement of about 50-100 hours at or below 7° C.

Pedigree and history: 'TH-1321' was selected in 2010 at Griffin, Ga., originating from a cross of 'TH-639' (non-patented breeding selection) X 'Rebel' (U.S. Plant Pat. No. 18,138) made in 2007 by D. Scott NeSmith. 'TH-1321' was first asexually propagated at Griffin, Ga. in 2010 by vegetative cuttings. The selection has been tested in plantings at a research farm at Alapaha, Ga., since 2011.

Observations have shown that the unique features of this new *Vaccinium corymbosum* 'TH-1321' are stable and have reproduced true to type in successive generations.

SUMMARY OF THE INVENTION

The new blueberry plant variety 'TH-1321' has not been observed under all possible environmental conditions. The phenotype may vary somewhat with variations in environment and cultural practices, such as temperature and light intensity, without, however, any variance in genotype.

The following traits have been repeatedly observed in Alapaha, Ga., and are determined to be the unique characteristics of the new blueberry plant variety 'TH-1321':

1. Large berry size;
2. Good berry flavor; and
3. Favorable berry firmness.

The new variety 'TH-1321' can be compared to the southern highbush blueberry varieties 'TH-819' (U.S. Plant Pat. No. 24,696) and 'Rebel' (U.S. Plant Pat. No. 18,138).

Comparison: The selection ripens with 'TH-819' and 'Rebel' in the early Georgia southern highbush season. 'TH-1321' has large, firm berries with good flavor as compared to 'TH-819' and 'Rebel' at Alapaha, Ga. over a 3-year period (Table 1). 'TH-1321' also has a lower chilling requirement compared to 'Rebel' and 'TH-639'.

TABLE 1

Table 1 sets forth three-year average ratings of some fruit and plant characteristics of 'TH-1321' and standard cultivars 'TH-819' and 'Rebel' from 2014-2016 in field test plots at Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2011.

| Berry and plant attributes | Alapaha location 'TH-819' | 'Rebel' | 'TH-1321' |
|---|---|---|---|
| Berry size | 7.2 | 7.7 | 8.8 |
| Berry scar | 7.3 | 7.5 | 7.3 |
| Berry color | 7.0 | 7.4 | 7.0 |
| Berry firmness | 7.0 | 7.5 | 8.8 |
| Berry flavor | 8.0 | 6.5 | 8.5 |
| Cropping | 3.4 | 6.0 | 1.5 |
| Plant vigor | 8.5 | 7.5 | 7.8 |
| Date of 50% flowering | Feb. 16 | Feb. 27 | Feb. 8 |
| Date of 50% ripening | April 24 | April 30 | April 19 |
| Fruit development period (days) | 67 | 62 | 68 |

BRIEF DESCRIPTION OF THE FIGURES

The accompanying photographic illustrations show typical specimens in full color of the foliage, flowering, and fruit of the new variety 'TH-1321'. The colors are as nearly true as is reasonably possible in a color representation of this type.

BOTANICAL DESCRIPTION

Figure 1A:
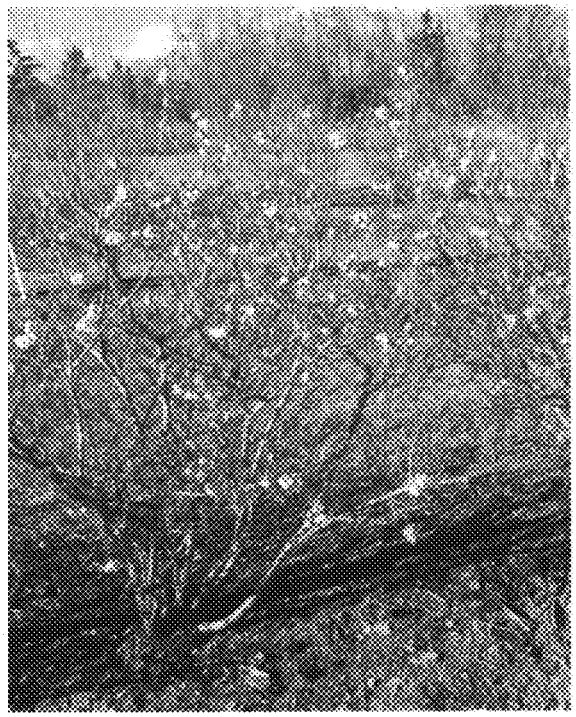
FIGS. 1A and 1B show photographs of the new variety 'TH-1321' during flowering at Alapaha, Ga.
Figure 1B:
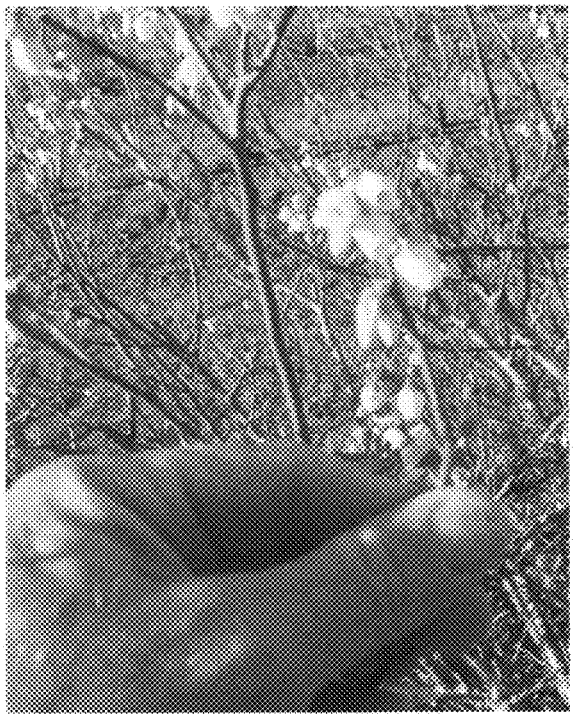
Figure 2:
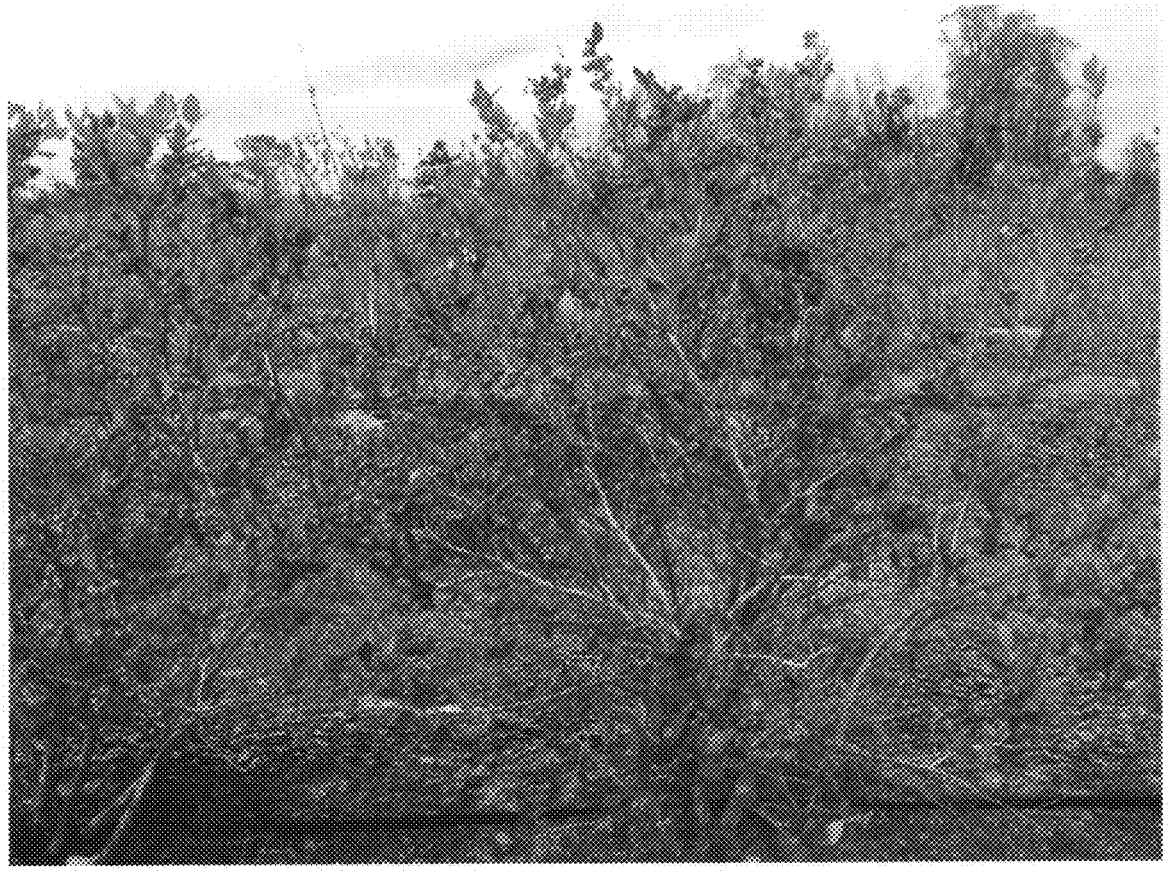
FIG. 2 is a photograph of the new variety 'TH-1321' 3-4 weeks prior to fruit ripening at Alapaha, Ga.
Figure 3:
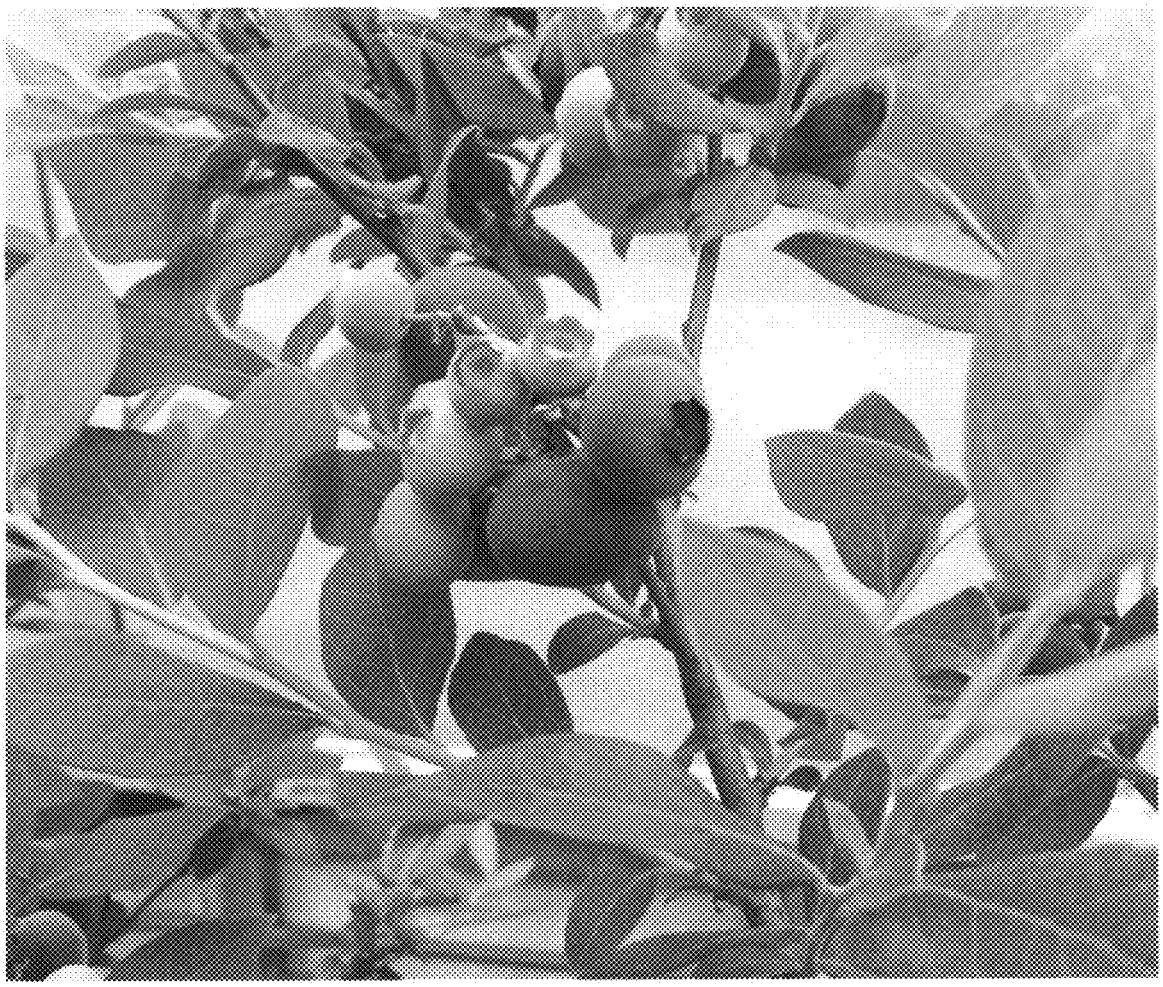
FIG. 3 is a close up photograph of fruit clusters of the new variety 'TH-1321'.
Figure 4A:
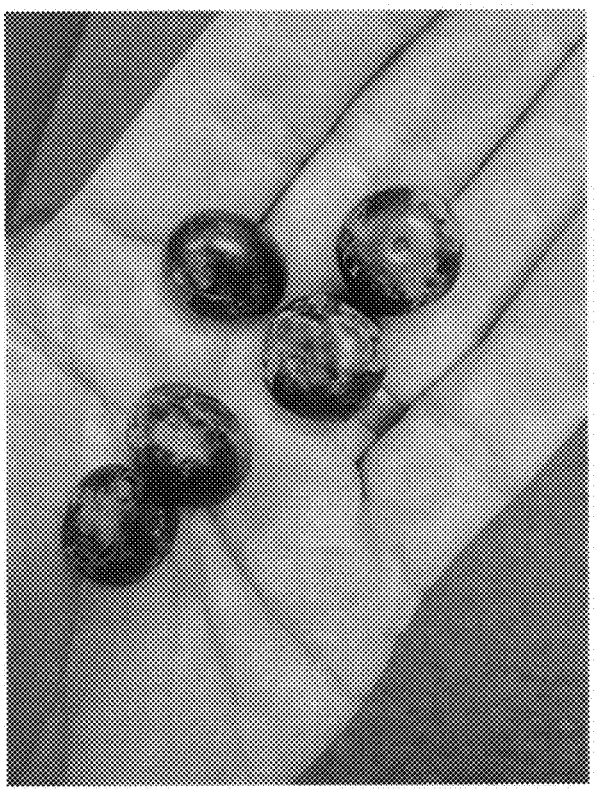
FIGS. 4A, 4B and 4C are photographs of harvested berries of the new variety 'TH-1321'; with 4C showing bisected berries.
Figure 4B:
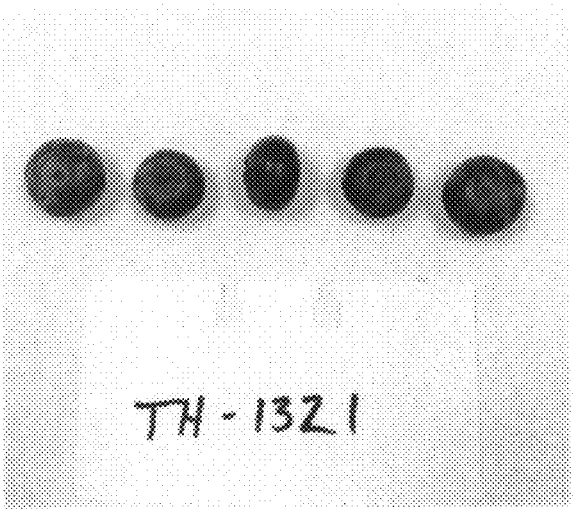
Figure 4C:
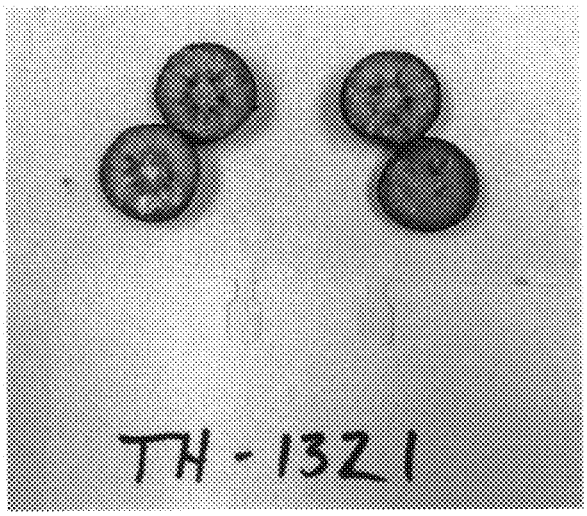

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical and pomological characteristics of the new variety 'TH-1321'. Where dimensions, sizes, colors, and other characteristics are given, it is to be understood that such characteristics are approximations and averages set forth as accurately as practicable. The descriptions reported herein are largely from specimen plants grown in Alapaha and Griffin, Ga., with supplemental irrigation. Plants were about 3 to about 6 years old.

Plant:

*Size.*—1.2 to 1.5 m tall by 3 years. Plants grown under highly productive soil and fertility conditions have exceeded 1.5 m tall in 4 years. The plant crown, or base, is narrow, typically 15 to 25 cm in diameter. The upper portion of the plant canopy reaches 1.2 to 1.5 m in diameter by 3 to 4 years.

*Growth habit.*—Plant is semi-spreading, with 4 to 7 main canes arising from the crown, and multiple branching of shoots from those canes above ground.

*Growth.*—Moderately to highly vigorous.

*Productivity.*—Medium to high crop and yield, averaging 5 to 8 lbs of fruit per plant each year for plants 4 years and older grown under well-fertilized and irrigated field conditions. Frost protection is required to reach yield potential due to early flowering.

*Cold hardiness.*—Although not tested except in portions of Georgia, the hardiness is believed to be similar to other early ripening southern highbush cultivars, such as 'TH-819' (U.S. Plant Pat. No. 24,696) and 'Rebel' (U.S. Plant Pat. No. 18,138).

*Chilling requirement.*—50-100 hours of temperatures at or below 7° C. (about 45° F.) to induce normal leafing and flowering during the spring under conventional production systems. The chill requirement is less than the male parent 'Rebel' (U.S. Plant Pat. No. 18,138; 300 to 350 hours of chilling required), and the female parent 'TH-639' (non-patented breeding selection; 150 to 250 hours of chilling required).

*Leafing.*—Plants tend to break sufficient leaf buds simultaneously with or shortly after anthesis.

*Fruiting wood.*—Moderate number of twigs 10 to 15 cm in length with internode lengths of 15 to 20 mm common.

*Canes.*—Diameter: Main cane base diameter 15 to 30 mm, two-year-old cane diameter 10 to 15 mm, current season wood diameter 3 to 5 mm. Color: RHS Brown Grey 201B for main cane, color transitioning from RHS Yellow Green 145A to RHS Greyed Orange 165A for two-year-old cane, and RHS Yellow Green 145A for current season wood.

*Disease resistance.*—No exceptional disease resistance or susceptibility observed; typical for early season southern highbush varieties 'TH-819' and 'Rebel'.

Foliage:

*Leaf color.*—Healthy mature leaves. Top side: Green RHS 137C. Under side: Yellow Green RHS 147C.

*Leaf arrangement.*—Alternate, simple.

*Leaf shape.*—Elliptic.

*Leaf surface.*—Glaucous.

*Leaf margins.*—Nearly entire; some slightly crenate.

*Leaf venation.*—Moderately reticulated.

*Leaf apices.*—Broadly acute.

*Leaf bases.*—Acute.

*Leaf dimensions.*—Length: 60.0 to 70.0 mm. Width: 30.0 to 35.0 mm.

*Petioles.*—Small. Length: Small, 3.0 to 5.0 mm long. Width: 1.5 to 2.0 mm. Color: Yellow Green RHS 145C.

Flowers:

*Date of 50% anthesis.*—3-year average Feb. 8 in southeast Georgia.

*Flower shape.*—Urceolate.

*Flower bud number.*—Medium to high, averaging 5 to 7 buds per fruiting shoot.

*Flowers per cluster.*—3 to 7 common.

*Flower fragrance.*—None.

*Corolla.*—Color: White 155C, some anthocyanins present in young flowers prior to opening give a tint of Red RHS 36A that rapidly transitions to White RHS 155C as corollas fully expand. Length: 9.5 to 10.5 mm. Width: 8.0 to 8.5 mm. Aperture width: 4.0 to 4.5 mm.

*Flower peduncle*.—Length: 7.5 to 9.0 mm. Color: Yellow Green RHS 145C.

*Flower pedicel*.—Length: 4.0 to 5.0 mm. Color: Green RHS 138C.

*Calyx* (*with sepals*).—Diameter: 7.0 to 7.5 mm. Color: Green RHS 138A center, Green RHS 138B sepals.

*Stamen*.—Length: 7.5 to 8.0 mm. Number per flower: 10. Filament color: Yellow Green RHS 145D.

*Style*.—Length: 9.0 to 9.5 mm. Color: Yellow Green RHS 145B.

*Pistil*.—Length: 11.0 to 12.0 mm. Ovary color (exterior): Green RHS 138B.

*Anther*.—Length: 4.0 to 5.0 mm. Number: 10. Color: Greyed Orange RHS 164A.

*Pollen*.—Abundance: Medium. Color: Yellow Orange RHS 18D.

*Self-compatibility*.—The cultivar has a moderate degree of self-compatibility.

Fruit:

*Date of* 50% *maturity*.—April 19 in southeast Georgia (3-year average).

*Fruit development period*.—68 days.

*Berry color*.—With wax: Blue RHS 102D. With wax removed: Black RHS 203C.

*Berry surface wax abundance*.—Medium.

*Berry flesh color*.—Green White RHS 157B.

*Berry weight*.—First harvest: 3.1 to 3.6 g. Second harvest: 2.2 to 2.6 g.

*Berry size*.—Height from calyx to scar: 14.0 to 17.0 mm. Diameter: 18.0 to 21.0 mm.

*Berry shape*.—Semi-disk shape.

*Fruit stem scar*.—Medium, medium dry, with little or no tearing upon harvest.

*Calyx*.—Depth very shallow, <1.0 mm; width large, 8.0 to 10.0 mm; sepals typically not highly visible, turned inward and when present, <<1 mm.

*Berry firmness*.—Very firm.

*Berry flavor and texture*.—Flavor is semi-sweet, mild acidic flavor; smooth texture.

*Storage quality*.—Very good.

*Suitability for mechanical harvesting*.—Unknown.

*Uses*.—Can be used as fresh fruit for shipping, but also processing markets.

Seed:

*Seed abundance in fruit*.—Medium, with 10 to 20 or more fully developed seeds per berry.

*Seed color*.—Greyed Orange RHS 165B.

*Seed dry weight*.—61.2 mg per 100 seeds.

*Seed size*.—1.9 to 2.2 mm long; 0.7 to 1.0 mm wide for fully developed seeds.

What is claimed is:

1. A new and distinct variety of southern highbush blueberry plant named 'TH-1321', as illustrated and described herein.

* * * * *